United States Patent

Gustafsson et al.

Patent Number: 6,156,951
Date of Patent: Dec. 5, 2000

[54] ABSORBENT STRUCTURE IN AN ABSORBENT PRODUCT SUCH AS AN ABSORBENT PANTS, DIAPER, INCONTINENCE PROTECTOR, SANITARY NAPKIN, PANTY LINER, DRESSING OR THE LIKE

[75] Inventors: Lars Gustafsson; Anette Buschka; Pia Kalentun, all of Gothenburg; Andrea Schmid, Molnlycke, all of Sweden

[73] Assignee: SCA Hygene Products Aktiebolag, Gothenburg, Sweden

[21] Appl. No.: 09/051,228

[22] PCT Filed: Oct. 3, 1996

[86] PCT No.: PCT/SE96/01250

§ 371 Date: Apr. 6, 1998

§ 102(e) Date: Apr. 6, 1998

[87] PCT Pub. No.: WO97/12573

PCT Pub. Date: Apr. 10, 1997

[30] Foreign Application Priority Data

Oct. 4, 1995 [SE] Sweden .................................. 9503442

[51] Int. Cl.[7] .............................. A61F 13/15; A61F 13/20
[52] U.S. Cl. .......................... 604/369; 604/370; 604/358; 604/374; 604/377; 604/378; 604/385.01; 604/385.14
[58] Field of Search ................................ 604/385.1, 383, 604/387, 369, 385.14, 385.01, 378, 377, 374, 370, 358

[56] References Cited

U.S. PATENT DOCUMENTS

| | | | |
|---|---|---|---|
| 2,064,431 | 12/1936 | Jurgensen | 604/385.1 |
| 2,551,663 | 5/1951 | Fox . | |
| 3,431,911 | 3/1969 | Meisel | 604/385.1 |
| 3,805,790 | 4/1974 | Kaczmarzyk et al. . | |
| 4,634,440 | 1/1987 | Widlund et al. | 604/383 |
| 5,010,595 | 4/1991 | Stradley | 2/227 |
| 5,030,229 | 7/1991 | Yang | 604/385.1 |
| 5,545,157 | 8/1996 | Van Iten | 604/385.1 |
| 5,624,423 | 4/1997 | Anjur et al. | 604/385.1 |
| 5,681,304 | 10/1997 | Van Iten | 604/387 |
| 5,785,698 | 7/1998 | Van Iten | 604/387 |
| 5,921,974 | 7/1999 | Kikuchi | 604/385.1 |

*Primary Examiner*—John G. Weiss
*Assistant Examiner*—Miley Craig Peppers, IV
*Attorney, Agent, or Firm*—Young & Thompson

[57] ABSTRACT

An absorbent structure in an absorbent product such as a diaper, an incontinence protector, a sanitary napkin, a panty liner or dressing, where the absorbent structure is formed of a piece of foamed material, which as an integrated unit has a liquid permeable surface and a corresponding surface which is liquid-proof and an absorbent layer between them. The liquid-proof surface can preferably be the skin of closed cells, which during manufacturing is formed on the piece of foamed material.

9 Claims, 4 Drawing Sheets

ABSORBENT STRUCTURE IN AN ABSORBENT PRODUCT SUCH AS AN ABSORBENT PANTS, DIAPER, INCONTINENCE PROTECTOR, SANITARY NAPKIN, PANTY LINER, DRESSING OR THE LIKE

BACKGROUND

An absorbent product such as an absorbent pants, a diaper, an incontinence protector, a sanitary napkin, a panty liner or a dressing usually comprises a liquid permeable top layer, a waterproof bottom layer and an absorption body arranged between them.

The top layer is the part of the absorbent product which faces towards the body of the user and the bottom layer is the part of the absorbent product which faces away from the body of the user. The material in the top layer is usually a perforated plastic film, a non-woven or a laminate of a plastic layer and a non-woven layer. The plastic material can be a thermoplastic, such as polyethylene. The non-woven material can be made of natural fibres, such as cellulose or cotton, or synthetic fibres, such as polyethylene, polypropene, polyurethane, nylon or regenerated cellulose.

The purpose of the top layer is an absorbent product of the above type is to lead the liquid into the product, prevent rewetting and in this manner form a dry surface against the skin of the user. A dry surface on the part of the product which lies against the skin of the user is important for comfort and to prevent skin irritation.

The bottom layer is manufactured in a liquid impermeable material. This is to prevent the leakage of liquid from the underside of the absorbent product. The bottom layer can be made of all types of material which fulfill the criterium of liquid impermeability and which have sufficient flexibility for this purpose. Examples of material suitable for the bottom layer are plastic films, non-wovens and laminates of these. The plastic film can, for example, be made of polyethylene, polypropene or polyester. An alternative name for the bottom layer is barrier layer.

The absorption body is usually made from cellulose pulp. It can be supplied in the form of rolls, bales or sheets which are dry defibrated and transferred in fluffed form to a pulp mat, occasionally with the mixing-in of so-called super-absorbent, which are polymers with the ability to absorb many times their own weight of water or body fluid.

The material in the absorption body can, as mentioned before, be cellulose fibres. Examples of other possible fibres are cotton fibres and synthetic fibres.

It is also known to use a foamed material in the absorption body.

Polymer foam with superabsorbent properties for use in absorbent products is described in, among others, EP 0 044 624 and U.S. Pat. No. 4,394,930. Polymer foam without superabsorbent properties for use in absorbent products is described in, among others, EP 0 163 150 and EP 0 229 122.

The problems with absorbent products with three or more layers is that they are expensive and technically difficult to manufacture. The last problem has become more and more apparent as machine speeds have increased during the years. A further problem with multi-layer products is that it is difficult to make three-dimensional body-fitting products. The shaping of the products is limited by the two-dimensional plastic films and non-woven layers which are available.

THE OBJECT OF THE INVENTION

The object of the invention is to manufacture an absorbent product which has the advantages of the above-mentioned multi-layer products, but which has a simplified manufacturing method and which can be given a three-dimensional shape.

DESCRIPTION OF THE INVENTION

The above-mentioned problem is solved according to the invention through the absorbent product comprising an absorbent structure which is made of a piece of foamed material which as an integrated unit has a liquid permeable surface intended during use to be facing towards the body of the user, a liquid-proof surface intended during use to be facing away from the body of the user and an absorption layer between them.

When a foamed material is moulded or extruded, it gets on its surface a skin which makes the product impervious. By the term skin it is meant that the cells on the surface of the foamed product are closed. Normally, this skin is cut-away in order to form an absorption body intended to be placed between a liquid permeable top layer and a liquid impermeable bottom layer.

According to the invention, the skin is retained and perforated only on the side which is intended to be worn against the body. In this way, a single layer product is attained which has the advantages of a three layer product, a liquid permeable surface facing towards the wearer, a liquid-tight outer surface facing away from the wearer, and an absorption body lying between them.

Manufacturing of the absorbent product according to the invention can, for example, be carried out by moulding or extruding.

In moulding, the material is injected into a mould of suitable, for example three-dimensional, shape, and is moulded there to its final shape. During the moulding, a skin forms on the product. According to the invention, the skin is retained on the surface of the absorbent product which during use shall be facing away from the user, while the surface intended to face towards the user is perforated.

During extrusion of the foamed material, a skin is also formed on the product. In order to achieve a three-dimensional product, the product achieved through extrusion is thermo-shaped.

During moulding or thermo-forming, the product manufactured from the foamed material can be shaped in the X-, Y- as well as the Z-direction. In this manner, in the case when the application concerns a child or adult diaper, a product is achieved which fits tightly in the groin of the user and especially applied elastic can be dispensed with. Naturally, in an analogous manner, a product according to the invention can be formed so that it fits the genitals of a woman, in the case of a sanitary napkin, a panty liner or a protection for lightly incontinent women, or the genitals of a man, in case of a protection for lightly incontinent men. In the case where the use concerns a dressing, it can naturally also be shaped according to need, for example according to the part of the body it is intended to be used on. Through moulding or thermo-forming a foamed product in this way, the folds which occur on conventional products can be avoided. Such folds are a common cause of leakage.

Perforation of the surface of the foamed absorption product which will be facing towards the body of the wearer can be brought about in different ways. Holes can for example be punched or cut with the aid of a mechanical cutting roller, ultrasound or laser. The perforated openings can be cylindrical, conical or elliptical. Preferably, the perforations have a successively diminishing cross-sectional dimension seen in the direction from the surface which during use is intended to be facing towards the user.

According to an alternative embodiment of the invention, the formed product, made for example by moulding or extrusion, can be divided into two, whereby two absorbent products are made. Because the largest pores occur in the middle of the originally shaped product, during this division, two products with a pore size gradient in the z-direction with the largest pores in the cut surface are formed. The products are then used so that the liquid permeable cut surfaces form the surface material on the product intended to be facing towards a wearer during use. Consequently, perforation of the surface is no longer necessary according to this embodiment.

The materials which can be used in a foamed products according to the invention include all materials which are suitable to be used in foamed absorption bodies, for example polystyrene, polyethylene, polyester, polyacrylates, cellulose or polyurethane.

In order to increase the retaining properties of the foam superabsorbent polymers can be inserted into the foam during manufacturing. For example, acrylic acid can be polymerized into the polyurethane when it is foamed.

When hydrophobic foam material is used, surface modifying is required in order to achieve a surface which is permeable for the fluids which the absorbent product according to the invention is intended for, above all urine and menstruation blood. Surface modifying can be achieved in different ways, among others through the addition of tensides to either the polymer melt or to the surface of the manufactured product, through plasma treatment, through corona treatment, through co-polymerization or through the admixture of other polymers.

An especially preferred use of the invention is as an absorption body in an absorbent pants as described in Swedish patent application 9500386-9. This describes an absorbent pants with a pants layer, also called inner pant, which can provide fastening of the product as well as a top layer thereof, at least partially. It is also possible to make holes in the pants layer corresponding to the body openings. In this case, the pants layer mainly functions as a fastening means for the absorbent product. In the application it is stated that the surface of the pants layer shall be bigger than the liquid-tight barrier layer facing away from the body of the user. When using the present invention, no barrier layer is required. The foamed product, according to the present invention, serves in this case both as absorption body and barrier layer. In the surface of the foamed product which is facing towards the body of the user, holes are made according to what has been described above or the originally foamed product is divided according to the above described method. The liquid impermeable skin on the side of the foamed product which during use is intended to be facing towards the user can also be cut away. An absorbent pants, according to what has been described above, is suitable as a pants sanitary napkin, that is to say for the absorption of blood, as well as a pants diaper, that is to say for urine and faeces absorption.

The invention shall be described more closely by way of embodiments and figures. The invention is not limited to the embodiments and the figures which are only intended to explain and illustrate the invention.

SHORT DESCRIPTION OF THE DRAWINGS

Figure 4A:
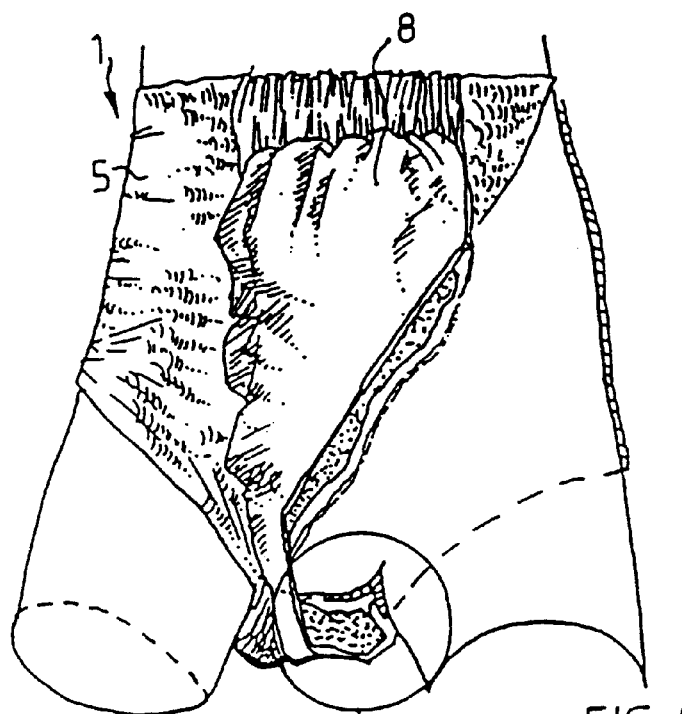
FIG. 4a shows an absorbent pants according to the invention seen from the front.
Figure 4B:
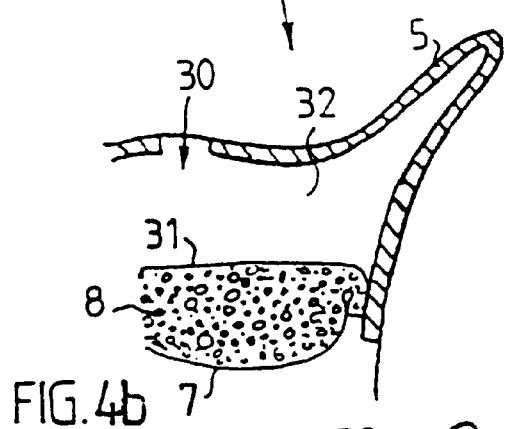
Figure 4C:
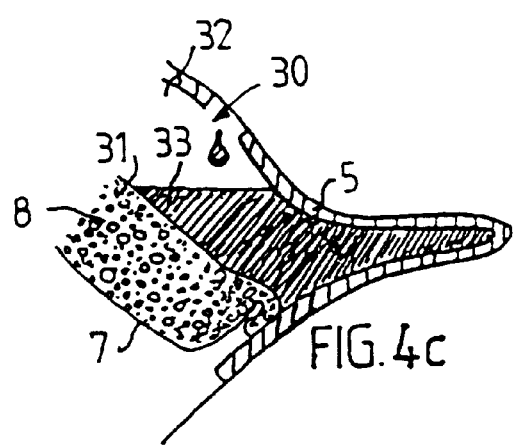
Figure 4D:
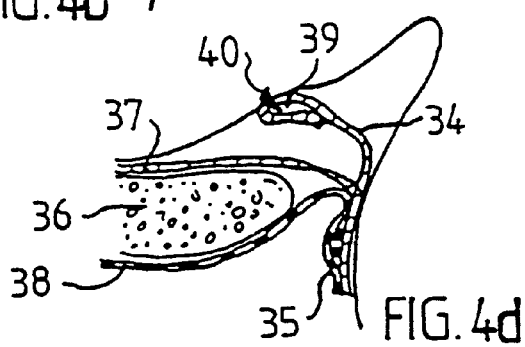

FIGS. 4b–d show in detail the crotch part of an absorbent pants according to the invention compared to a prior art diaper.

Figure 5:
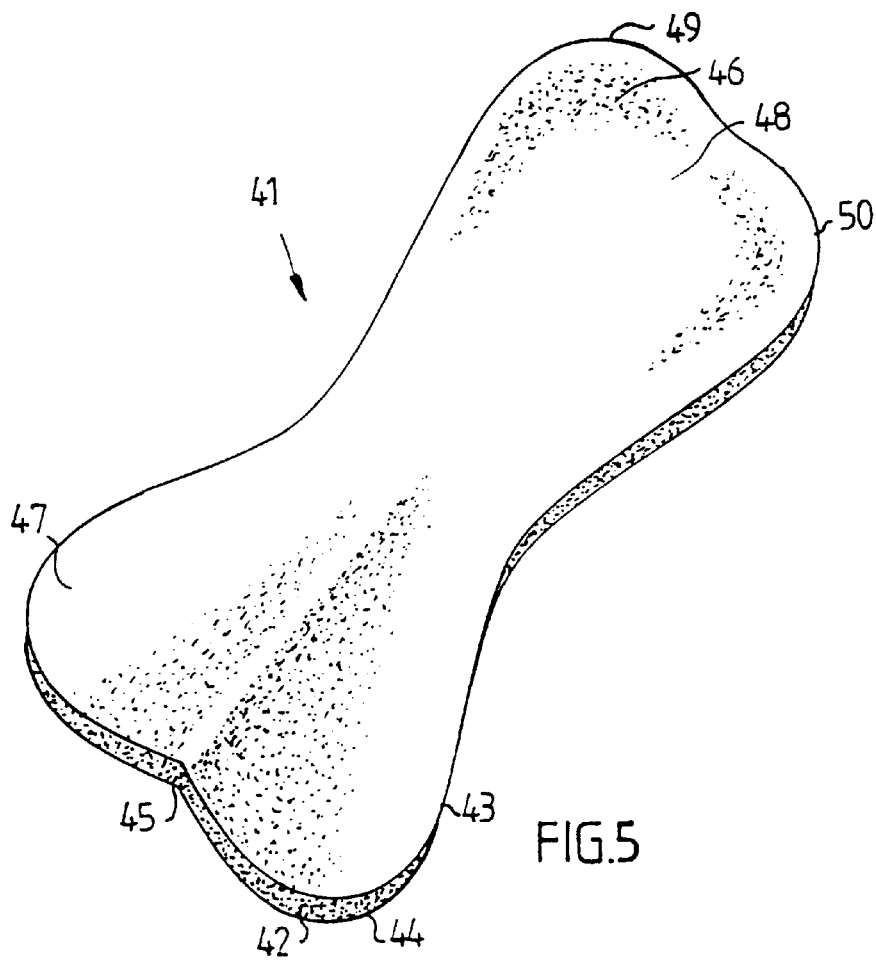

FIG. 5 shows a three-dimensionally formed sanitary napkin according to the invention.

Figure 6:
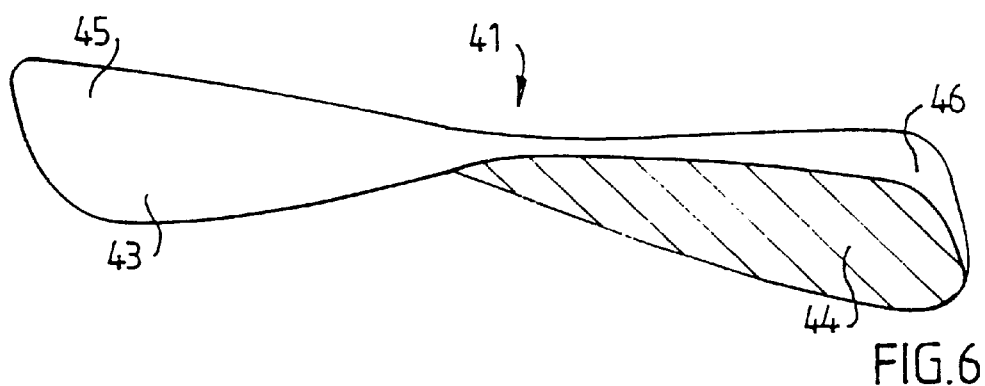

FIG. 6 shows a three-dimensionally shaped sanitary napkin according to the invention seen from a long side.

Figure 7:
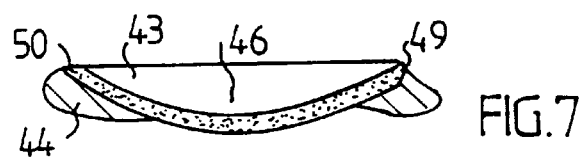

FIG. 7 shows a three-dimensionally shaped sanitary napkin according to the invention seen from a short side.

Figure 8:
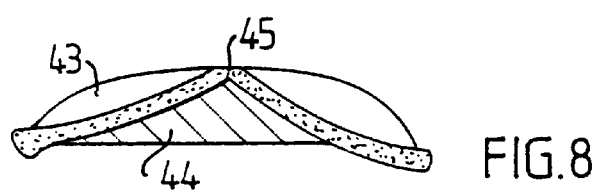

FIG. 8 shows a three-dimensionally shaped sanitary napkin according to the invention seen from the opposite short side shown in FIG. 7.

Figure 9:
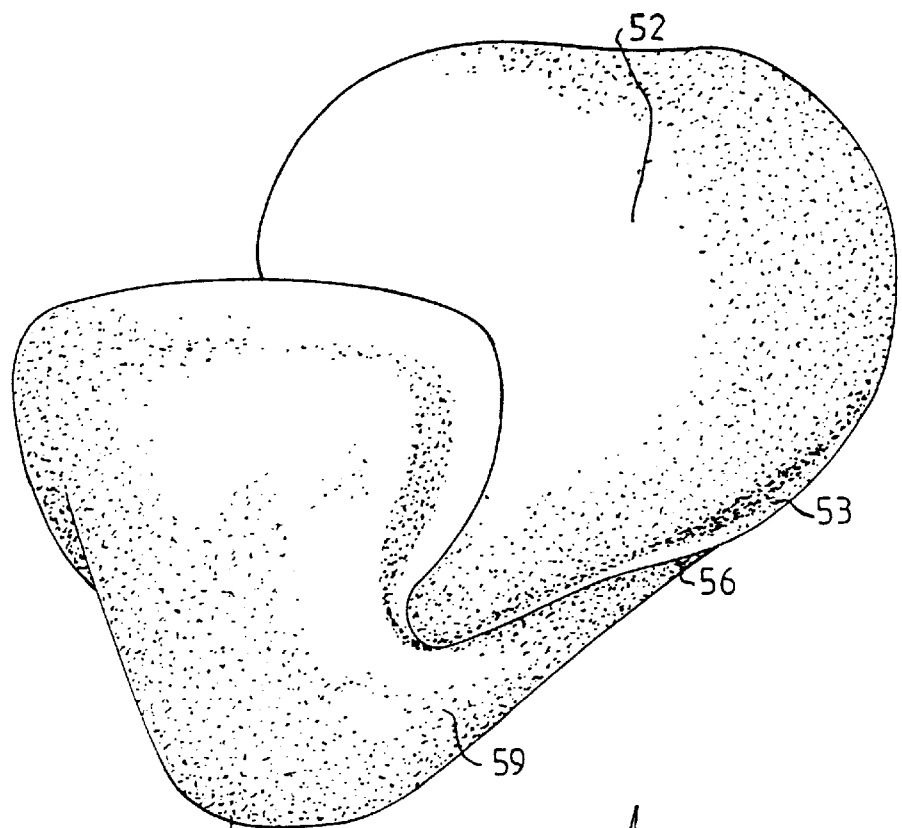

FIG. 9 shows a three-dimensionally shaped adult diaper according to the invention.

Figure 10:
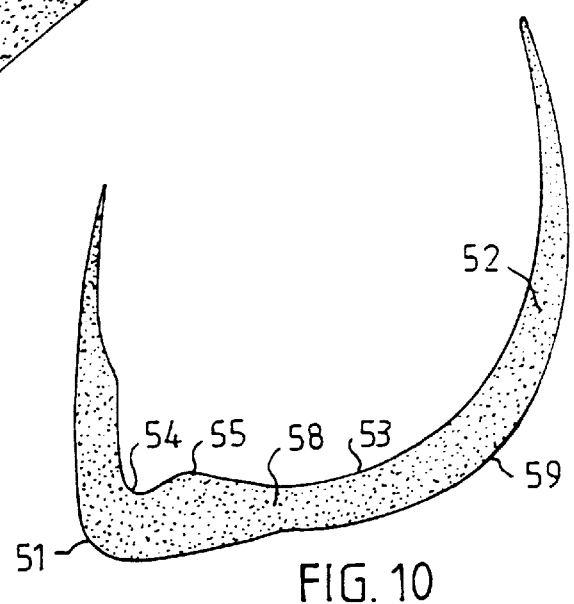

FIG. 10 shows the three-dimensionally shaped adult diaper of FIG. 9 seen from a long side.

Figure 11:
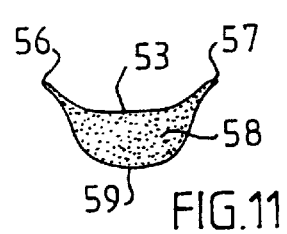

FIG. 11 shows the three-dimensionally shaped adult diaper of FIG. 9 seen from a short side.

DESCRIPTION OF THE FIGURES AND THE EMBODIMENTS

Figure 1:
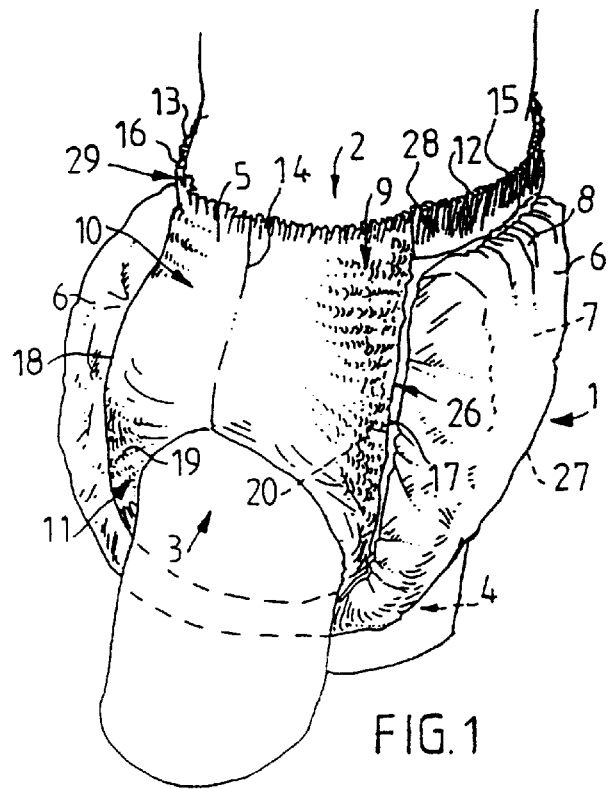
FIG. 1 shows an absorbent pants according to the invention placed on a wearer seen at an angle from in front.

FIG. 1 shows an absorbent pants 1 worn by an imaginary user, having a waist opening 2 and two leg openings 3 and 4, of which one, however, is hidden in the Figure. The pants comprises a pants layer 5 and outside this is arranged a material body 8, which functions as an absorption unit 6 as well as a barrier layer 7, in accordance with what has been described earlier.

The pants layer 5 faces towards the body of the user and lies in contact with this over essentially the whole of its surface. The pants layer is joined together by two side seams, one in each respective side, of which only one 14 is visible in FIG. 1. The side seams extend from the waist opening 2 to the respective leg openings 3, 4. The pants layer 5 further comprises a front and a rear waist part, 9 and 10. These waist parts surround together the stomach and back side, respectively, of the user. Between the two waist parts 9 and 10, the pants layer 5 has a crotch part 11.

The two waist parts have each an end edge 12 respectively 13.

The pants layer 5 is elastic, FIG. 1 shows an example of an elastic pants layer, which comprises an elastic means 20 and at least one essentially inelastic material layer 19. The elastic means 20 is attached in a pre-tensioned state to the essentially inelastic material layer 19. The piece of foamed material 8 has end and side edges 15, 16, and 17, 18, respectively. The end edges 15, 16 joined with the pants layer 5 in regions 28, 29 thereof which extend from the end edges 12, 13, respectively, of the pants layer and a short distance inwardly in the direction of the crotch part 11. The side edges 17, 18 are joined to the pants layer 5 in the regions 26, 27 between the respective side edges which in the joined-together configuration form the side seam 14.

Figure 2:
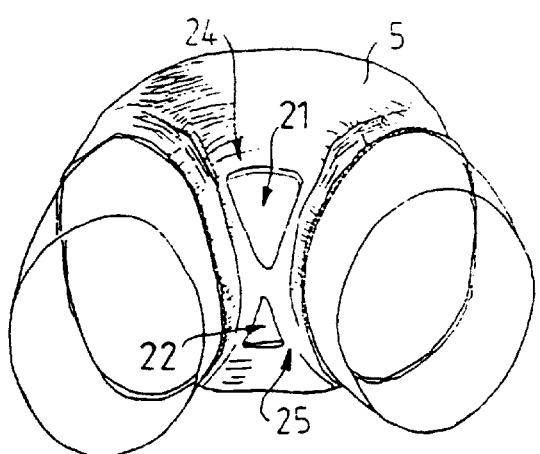
FIG. 2 shows an absorbent pants according to the invention placed on a wearer seen from below.
Figure 3:
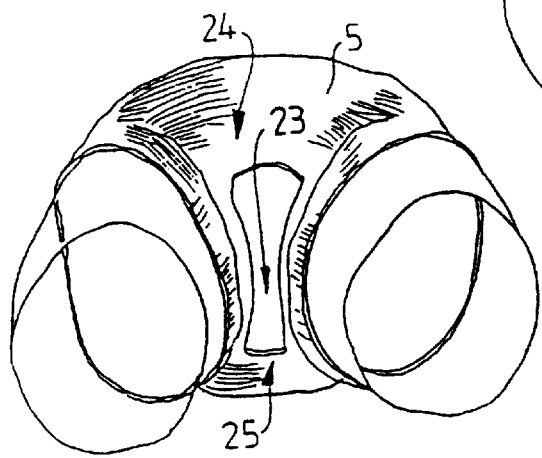
FIG. 3 shows an absorbent pants, according to another embodiment of the invention than that shown in FIG. 2, placed on a wearer seen from below.

FIGS. 2 and 3 show two different embodiments of the absorbent pants according to the invention. The pants layer 5 is equipped with one or more openings for the passage of urine, faeces or menstruation fluid. FIG. 2 shows an embodiment with two openings for the passage of urine/faeces/menstruation fluid: a front opening 21 in the front part 24 of the crotch part 11 and a rear opening 22 in the rear part 25 of the crotch part 11.

FIG. 3 shows an embodiment of the absorbent pants according to the invention, which has an opening 23 which extends from the front part 24 to the rear part 25 of the crotch part 11 for the passage of urine/faeces/menstruation fluid.

FIG. 4a shows an absorbent pants of the same type as shown in FIG. 1. The pants 1 is shown from in front in its intended position of use on a user indicated by whole and dashed lines. Part of the pants is shown in cross-section and another part of the pants is circled and shown magnified in FIG. 4b.

FIGS. 4a and 4b show how the pants layer 5 lies in contact with the body of the user and follows up into the fold of the groin. The pants layer 5 is shown interrupted by the opening 30. FIG. 4b also shows an absorption body 8 made of foamed material having a liquid permeable surface 31 on the side facing towards the pants layer 5. A pocket 32 is formed between the pants layer 5 and the absorption body 8.

FIG. 4c shows how urine or menstruation fluid 33 has entered into the pocket 32 through the opening 30 and has not yet been able to pass through the liquid permeable surface 31 on the absorbent body 8. This is not an abnormal situation, as the absorbent pants often slope when the user lies on one side or bends in one way or another. Therefore, in the position shown, the absorption body 8 has not been able to suck in the fluid in the intended manner, but this has instead collected in the completely closed corner of the pocket 32. Nothing at all can leak out, as the pants layer 5 is hydrophobic and the outer surface 7 of the absorption body 8 is waterproof.

As a comparison with the present invention, FIG. 4d shows an example of a known raised leakage barrier for a diaper. The known leakage barrier 34 is made of a separate piece of material arranged on an elastic leg margin 35. The diaper comprises in the normal way an absorption body 36, a liquid permeable covering layer 37 and an outer barrier layer 38. The leakage barrier 34 comprises an elastic means 39 with the help of which it can be lifted up from the liquid permeable covering layer 37.

The outer barrier layer 38 forms the completed diapers "pants-forming" layer and is therefore the layer which supports the loads on the diaper. In this way, the outer barrier layer can move in relationship to the user when it is affected by forces. Because the leakage barriers are connected to the outer layer, this also can move in relation to the user. The leakage barrier 34 can therefore be forced to release its contact against the user or be moved in the transverse or longitudinal direction out of its intended place on the user. Because the leakage barrier 34 has only a very narrow contact line 40 facing the user, liquid can very quickly pass the leakage barrier as soon as it loses contact with the user.

The advantage with an absorbent pants according to the present invention as compared to an absorbent pants according to Swedish patent application 9500386-9, is that the absorption body 8, the liquid permeable layer 31 and the liquid-proof barrier layer 7 are formed of the same piece of material in a construction according to the present invention. This gives advantages during manufacturing. It is easier and faster to manufacture the absorbent pants with less parts. With just one piece of material to work with, it is also considerably easier to form three-dimensional structures which fit on the pants layer in the absorbent pants. This means that it is also easier for the absorbent pants to achieve a good fit against the anatomy of a possible user.

FIG. 5 shows another embodiment of the present invention, a sanitary napkin 41. This construction is also suitable as an incontinence protector for lightly incontinent people. The sanitary napkin 41 consists of a single foamed piece of material which has an absorbent part 42, an upper liquid permeable surface 43 and a liquid-proof rear side 44.

It is possible within the scope of the invention that the sanitary napkin not only consists of a piece of foamed material but that the liquid permeable surface 43 which during use is intended to be facing towards the body of the user, is made of a separate liquid permeable layer. This naturally takes away a part of the simplicity of the invention, but in certain cases it can be desirable to have a surface material with special properties, which can not be achieved during working of the piece of foamed material. The separate surface material 43 can, for example, be made of a perforated plastic film or a non-woven layer.

FIGS. 5–8 show the three-dimensional shaping which can be achieved in a sanitary napkin according to the present invention. In order to achieve a body-fitting three-dimensional structure in the napkin and in this way prevent leakage when the user is lying down or moves, the napkin is foamed with a ridge 45 in one end 47 and a bowl-shaped appearance 46 in the other end 48.

During use, the short side 47, which is equipped with the ridge 45, if intended to be placed rearwardly on the user. The ridge 45 fits in the gap between the buttocks of the user and presents leakage when the user sits down or lies on her back.

The ridge 45 is highest at the short side 47 of the napkin and decreases towards the middle of the napkin in the longitudinal direction. The total length of the ridge 45 lies normally between ⅙ and ½ of the total length of the napkin. Preferably, the ridge 45 is between ⅕ and ⅓ of the length of the napkin. With a total napkin length of 15 cm, the ridge can have a length of between 3 and 7.5 cm, preferably between 3 and 5 cm. In the case when the napkin is 20 cm long in total, the ridge 45 could have a length of between 3.3 and 10 cm, preferably between 4 and 6.7 cm.

The opposing short side 48 to that which has the ridge 45 has, as mentioned earlier, a bowl-shaped appearance 46. This is achieved through the corners of the napkin 49, 50 on the short side 48, during manufacture of the napkin, being made so that they are turned up somewhat towards the surface 43 of the napkin which is intended to be worn against the body. The bowl-shape 46 of the short side 48 is intended to fit against the body of the user and prevent forward leakage. This can otherwise occur when the user lies on her stomach or in some other way leans forwards.

FIG. 6 shows a sanitary napkin 41 according to the invention seen from one of the long sides. The dashed regions show the liquid-proof rear side 44 and the un-dashed regions show the liquid permeable front side 43 of the piece of foamed material.

FIG. 7 shows a sanitary napkin according to the invention, seen from the short side 48, which has a bowl-shape 46 formed by the turned up corners 49 and 50.

FIG. 8 shows a sanitary napkin according to the invention, seen from the short side 47, which has a ridge 45.

FIGS. 9–11 show yet another embodiment of the present invention, a three-dimensionally shaped adult diaper. This embodiment is naturally equally suitable for children's diapers.

The diaper has a part 51 intended to face towards the stomach of the user, that is to say the front part 51 shall lie against the lower part of the abdomen of the user. The diaper has also a part 52 intended to face towards the back of the user, that is to say to lie against the buttocks of the user The front part 51 is, seen from the surface 53 of the diaper which during use is intended to face towards the user, bowl-shaped so that it fits the space around the groin of the user and the rear part 52 has a wider and flatter bowl shape than the front part 51 so that the part 52 should fit around the buttocks of the user. The front part 51 has, seen from one of the long sides, a recess 54 and a raised portion 55 in order to fit better against the genitals of the user. FIG. 11 shows the diaper seen from one of the short sides, more accurately from the rear part 52. This drawing illustrates how the edges 56 and 57 of the diaper have a flange-like appearance in order to fit against the groin of the user and in the changeover between the legs and the lower abdomen of the user. It is extremely important that a diaper fits in this region for security against leakage.

The adult diaper has, in addition to the liquid permeable surface 53 facing towards the user, an absorption part, known also as the absorption layer 58, and a water proof surface 59 facing away from the user.

The invention is naturally not limited to the embodiments shown. The shape of the product including the three-dimensional shape can be varied in order to achieve an optimal anatomical fit for each intended field of use. The invention can also be applied to, for example, wound dressings.

What is claimed is:

1. An absorbent structure for use in an absorbent product selected from the group consisting of an absorbent pants, a diaper, an incontinence protector, a sanitary napkin, a panty liner and a dressing, the absorbent structure comprising a liquid permeable surface intended to be facing towards the body of a wearer during use, a liquid-proof surface intended during use to face away from the body of the wearer and an absorption layer between them, wherein the absorbent structure consists of single piece of foamed material, having as an integrated unit the liquid permeable surface, the liquid-proof surface and the absorption layer therebetween.

2. The absorbent structure according to claim 1, wherein the liquid-proof surface is the skin of closed cells which during manufacturing is formed on the piece of foamed material.

3. The absorbent structure according to claim 1, wherein the liquid permeable surface is the skin of closed cells which during manufacturing is formed on the piece of foamed material and which is perforated in connection with the manufacturing of the piece of material.

4. The absorbent structure according to claim 3, wherein the perforating have a successively diminishing cross-section seen in the direction from the surface which during use is intended to face towards the user.

5. The absorbent structure according to claim 1 wherein the piece of foamed material has a three-dimensional shape.

6. The absorbent structure according to claim 1, wherein the piece of foamed material is manufactured from polyurethane.

7. The absorbent structure according to claim 1, wherein the liquid permeable surface is formed of a cut surface, which is formed when the structure is divided in the longitudinal direction.

8. An absorbent pants comprising an inner pants, which during use in its entirety conforms in shape to, and lies against, the skin of the user, and an absorbent structure, wherein the absorbent structure is formed from a piece of foamed material according to claim 1.

9. An absorbent product selected from the group consisting of a sanitary napkin, a panty liner and an incontinence protector, which has two long sides and two short sides, wherein the absorbent product is made of a single piece of foamed material and has a three-dimensional shape with a bowl-shaped appearance on one short side intended to be worn forwardly and nearest to a wearer and a raised back on the short side intended to be worn rearwardly and nearest to the wearer.

* * * * *